United States Patent [19]
Akashi et al.

[11] Patent Number: 5,821,108
[45] Date of Patent: Oct. 13, 1998

[54] ENRICHMENT FOR A THYMOCYTE SUBSET HAVING PROGENITOR CELL ACTIVITY USING C-KIT AS A SELECTION MARKER

[75] Inventors: Koichi Akashi, Palo Alto; Irving Weissman, Redwood City, both of Calif.

[73] Assignee: The Board of Trustees of the Leland Stanford Junior University, Palo Alto, Calif.

[21] Appl. No.: 418,534

[22] Filed: Apr. 7, 1995

[51] Int. Cl.$^6$ .................. C12N 15/85; G01N 33/53; A61K 39/395

[52] U.S. Cl. .................. 435/240.2; 435/7.24; 424/93.71; 424/140.1; 424/143.1; 424/154.1; 530/388.75

[58] Field of Search ............... 530/389.6, 391.3, 530/413, 388.22, 388.75; 424/93.71, 140.1, 143.1, 152.1, 172.1, 173.1, 154.1; 435/7.24, 240.2

[56] References Cited

FOREIGN PATENT DOCUMENTS 10293   4/1994   WIPO .

OTHER PUBLICATIONS

Majundar et al. 1990 J. Immnology vol. 144, No. 1,:111–121.
Ashman et al. 1991 Blood vol. 78, No. 1, 30–37.
Adkins et al. (1987) *Ann. Rev. Immunol.* 5:323.
Besmer et al. (1986) *Nature* 320:415–421.
Chabot et al. (1988) *Nature* 335:88–89.
Chan et al. (1994) *Semin Immunol* 6:241–248.
Fowlkes and Pardoll (1989) *Adv. Immunol.* 44:207.
Guidos et al. (1990) *J. Exp. Med.* 172:835–845.
Ikuta and Weissman (1992) *P.N.A.S.* 89:1502–1506.
Kraft et al. (1993) *J.E.M.* 178:265–277.
Moore et al. (1994) Immunology 81:115–119.
Morrissey et al. (1994) *Cell Immunol* 157:118–131.
Okada et al. (1991) *Blood* 78:1706–1712.
Terstappen et al. (1992) *Blood* 79:666.
Veis et al. (1993) *J. Immunol* 151:2546–2554.
Wolf and Cohen (1992) *Immunology* 77:362–368.
Wu et al. (1991) *Nature* 349:371.
Tatsumi et al. (1990) P.N.A.S. 87:2750–2754.
Denning et al. (1989) J. Immunol. 142:2988–2997.

*Primary Examiner*—Christine M. Nucker
*Assistant Examiner*—Julie E. Reeves
*Attorney, Agent, or Firm*—Pamela J. Sherwood; Fish & Richardson P.C.

[57] ABSTRACT

A subpopulation in the CD4$^+$8$^+$ (DP) thymic blast population is identified that is the precursor for thymic T cells. All such progenitors are c-kit$^+$. The c-kit$^+$ subset expresses lower levels of CD4 and CD8 than the large and small DP c-kit– cells. These DP$^{int}$ c-kit$^+$ cells differentiate to thymic T cells rapidly on heterogenous thymic stromal cell cultures. Similar maturation takes place in vivo over 4 days. A method for isolating the cells which are c-kit$^+$ and which express intermediate or low levels of CD4+/CD8+ is also disclosed.

8 Claims, 9 Drawing Sheets

FIG. 6E

ENRICHMENT FOR A THYMOCYTE SUBSET HAVING PROGENITOR CELL ACTIVITY USING C-KIT AS A SELECTION MARKER

CROSS-REFERENCE TO GOVERNMENT GRANTS

Research performed in support of this application was supported in part by USPHS grant CA-42551. The U.S. government may have rights in any patent issuing on this application.

INTRODUCTION

1. Technical Field

The field of this invention is the application of thymocyte subset populations.

2. Background

T lymphocytes compose a major part of the body's immune defenses against bacterial, viral and protozoal infection, and have been implicated in the rejection of cancerous cells. Numerous autoimmune syndromes have been linked to antigen-specific T cell attack on various parts of the body. Conversely, immunodeficiencies are generally related to a lack of functional T cells. AIDS, in particular, is a result of the destruction of $CD4^+$ T cells by HIV-1.

The thymus is the major site of differentiation of T-cells. Bone marrow- or fetal liver-derived thymic progenitors migrate to the thymus where they undergo rapid proliferation and differentiation in a process known as thymic maturation. In the thymus, under the influence of the thymic stromal microenvironment, immature thymocytes acquire various cell surface molecules useful in their future role as mature T cells. The expression of the MHC antigen co-receptors CD4 and CD8, and the T-cell receptor (TCR) α-β or γ-δ heterodimers that are associated with the invariant CD3 polypeptides has been previously characterized.

Based on expression of CD4 and CD8, thymocytes have been divided into four categories: $CD4^-8^-$ (double negative, DN), $CD4^+8^+$ (double positive, DP), $CD4^+8^-$ and $CD4^-8^+$ (single positives, SP). The immature $CD3^-4^-8^-$ cells contain a subpopulation that gives rise to $CD3^{lo}4^+8^+$ thymocytes, before differentiating to functionally mature $CD3^{hi}4^+8^-$ and $CD3^{hi}4^-8^+$ T-cells. During the process of thymic education, maturing T-cells acquire the property of responsiveness to foreign antigens presented in association with self-MHC molecules by the antigen presenting cells (positive selection) and of tolerance or non-responsiveness to self antigens (negative selection).

Only 1 to 4% of thymocytes survive selection and progress to become mature T cells. The majority become small DP cells and are destined for intrathymic death. It is believed that death is the result of failing either positive or negative selection. It is critical for proper immune function to have T cells that are both responsive to foreign antigens and tolerant to self. The thymocyte subset that is the subject of the selection process is therefore of great interest.

It is of further interest to be able to grow T-cells at various stages of differentiation, to investigate the various interactions associated with such maturation or selection, the factors involved in such maturation and selection, to evaluate cells as T-cell precursors, and to be able to grow T-cells, which may find use in therapy for the treatment of various diseases.

RELEVANT LITERATURE

Thymic maturation is described by Adkins et al. (1987) *Ann. Rev. Immunol.* 5:323; Fowlkes and Pardoll (1989) *Adv. Immunol.* 44:207; and Guidos et al. (1990) *J. Exp. Med.* 172:835–845. A description of the thymus structure may be found in van Ewijk (1991) *Ann. Rev. Immunol.* 9:591. Expression of CD4 in thymic progenitors is discussed in Terstappen et al. (1992) *Blood* 79:666 and Wu et al. (1991) *Nature* 349:71. A model for positive selection in the thymus is presented in Chan et al. (1994) *Semin Immunol* 6:241–8.

Methods for the culture of thymocytes on heterogeneous thymic stromal cells are described in International application PCT/US93/09322. Methods for the culture of thymocytes in the SCID-hu mouse are described in Kraft et al. (1993) *J. E. M.* 178:265–277.

Developmental regulation of Bcl-2 expression in the thymus is described in Moore et al. (1994) *Immunology* 81:115–9. The susceptibility of thymocytes to apoptosis may be influenced by the expression of Bcl-2, a proto-oncogene known to increase the resistance to apoptosis in various cell systems. Expression of the Bcl-2 protein in the thymus is disclosed in Veis et al. (1993) *J Immunol* 151:2546–54. Bcl-2 was expressed in nearly all CD4+ and CD8+, and CD3hi cells, but in only 5 to 10% of CD4+8+ cells. It is suggested that early double negative thymocytes express Bcl-2 but lose Bcl-2 with differentiation to the double positive stage. Bcl-2 expression is regained during selection to a single positive state.

Steel factor (c-kit ligand) is shown to stimulate the in vitro growth of immature $CD3^-CD4^-CD8^-$ thymocytes and to synergize with IL-7 in Morrissey et al. (1994) *Cell Immunol* 157:118–31. Expression of cytokines and their receptors by human thymocytes and thymic stromal cells is described in Wolf and Cohen (1992) *Immunology* 77:362–8.

The expression of c-kit on mouse hematopoietic progenitor cells is discussed in Ikuta and Weissman (1992) *P.N.A.S.* 89:1502–1506; and Okada et al. (1991) *Blood* 78:1706–1712. Background on the c-kit gene can be found in Besmer et al. (1986) *Nature* 320:415–421; and Chabot et al. (1988) *Nature* 335:88–89.

SUMMARY OF THE INVENTION

Two substantially enriched thymocyte subpopulations having progenitor cell activity are provided. Methods are provided for the isolation and culture of the subpopulations. The cell enrichment methods employ reagents that specifically recognize c-kit protein, in conjunction with other markers that discriminate between thymocyte subsets. The subject thymocyte subpopulations are the object of thymic selection, and are the progenitor cells for mature T cells.

DESCRIPTION OF THE SPECIFIC EMBODIMENTS

Two substantially enriched thymocyte subpopulations are provided, having progenitor cell activity for differentiation in the T lineage. Methods are provided for the isolation and culture of the subpopulations. The subject cells are separated by selection for cells expressing c-kit protein. Other markers useful for enrichment of the subject thymocyte subpopulation are CD8, CD4 and CD3. The enriched cells differentiate into T cells when cultured on heterogenous thymic stromal cell cultures, or when injected in vivo.

The subject cell populations are characterized by the ability to differentiate and expand in vitro and in vivo into mature T cells that recognize MHC class II molecules, usually CD4$^+$, and T cells that recognize MHC class I molecules, usually CD8$^+$. Unlike the hematopoietic stem cell, the subject populations are committed to the T lineage. The subject T cell progenitor populations are useful for transplantation into recipients with immunodeficiencies involving T cells, e.g. AIDS, SCID, etc. and for transplantation in conjunction with pluripotential hematopoietic stem cells to recipients requiring hematopoietic reconstitution, e.g. following cytoreductive chemotherapy or radiotherapy. The cells are useful in vitro in screening assays to define growth and differentiation factors, and receptors involved in T cell development and regulation. The role of the subject cell population as the object of thymic selection allows identification of factors and receptors that are important in the development of T cell tolerance to self, and reactivity to foreign antigens.

A method for enrichment for two substantially pure thymocyte subpopulation having T cell progenitor activity are provided. The enriched cell populations will usually have at least about 90% cells of the selected phenotype, more usually at least 95% cells of the selected phenotype. The subject cell populations are separated from other thymocytes on the basis of specific markers, which are identified with affinity reagents, e.g. monoclonal antibodies.

Thymocytes, as known in the art, shall be intended to mean lymphoid cells of the T lineage that are undergoing differentiation in the thymus. Generally excluded from the term are fully mature T cells and B cells present as a result of peripheral blood circulation through the thymus, thymic epithelial cells and thymic dendritic cells. The thymocytes may be obtained from any mammalian species, e.g. equine, bovine, canine, feline, rodent, e.g. mice, rats, hamster, primate, etc., particularly human. The source of thymocytes may be fresh thymus tissue, obtained by biopsy from a live donor or obtained from a dead or dying donor within about 48 hours of death, or freshly frozen tissue, tissue frozen within about 12 hours of death and maintained at below about –10° C., usually at about liquid nitrogen temperature (–70° C.) indefinitely. The cells may be fetal, neonate, adult.

As an alternative source of cells, hematopoietic stem cells or commited T lineage progenitors derived thereof, as described in U.S. Pat. No. 5,061,620, issued on Oct. 29, 1991 may be cultured in vivo or in vitro to provide a source of thymocytes. The thymus tissue may be from an organ implanted in a chimeric host, particularly a thy/liv xenograft, as described in European Patent application 91.113061.5. The tissue obtained from the chimeric host may be treated analogously to the tissue obtained from a natural source.

The subject thymocytes are characterized as expressing c-kit (CD117) on their cell surface. Antibodies that specifically bind c-kit in humans, mice, rats, etc. are known in the art. Alternatively, the c-kit ligand, Steel factor (Slf) may be used to identify cells expressing c-kit.

The first subset of subject cells also have the phenotype of expressing intermediate levels of CD4 and CD8 on the cell surface (double positive, DP$^{int}$), are CD44 positive, heat stable antigen (HSA) positive, are in the largest 20% of thymocytes for cell size, and have low level expression of CD3, indicating functional gene rearrangement of the T cell receptor alpha and beta locus. The intermediate designation indicates that the level of staining is above the brightness of an isotype matched control, but is not as intense as the most brightly staining cells in the thymus. In a separation procedure combining selection for c-kit$^+$ cells, it is not necessary to distinguish between DP$^{int}$ and DP$^{hi}$ staining, because the DP$^{hi}$ cells are c-kit negative.

Similarly, a more primitive progenitor population comprises large cells that express low levels of CD4 and CD8 (DP$^{lo}$), and are c-kit$^+$. The cells are the progenitors of the large DPintc-kit+ progenitors, and therefore share developmental outcomes.

Figure 1:
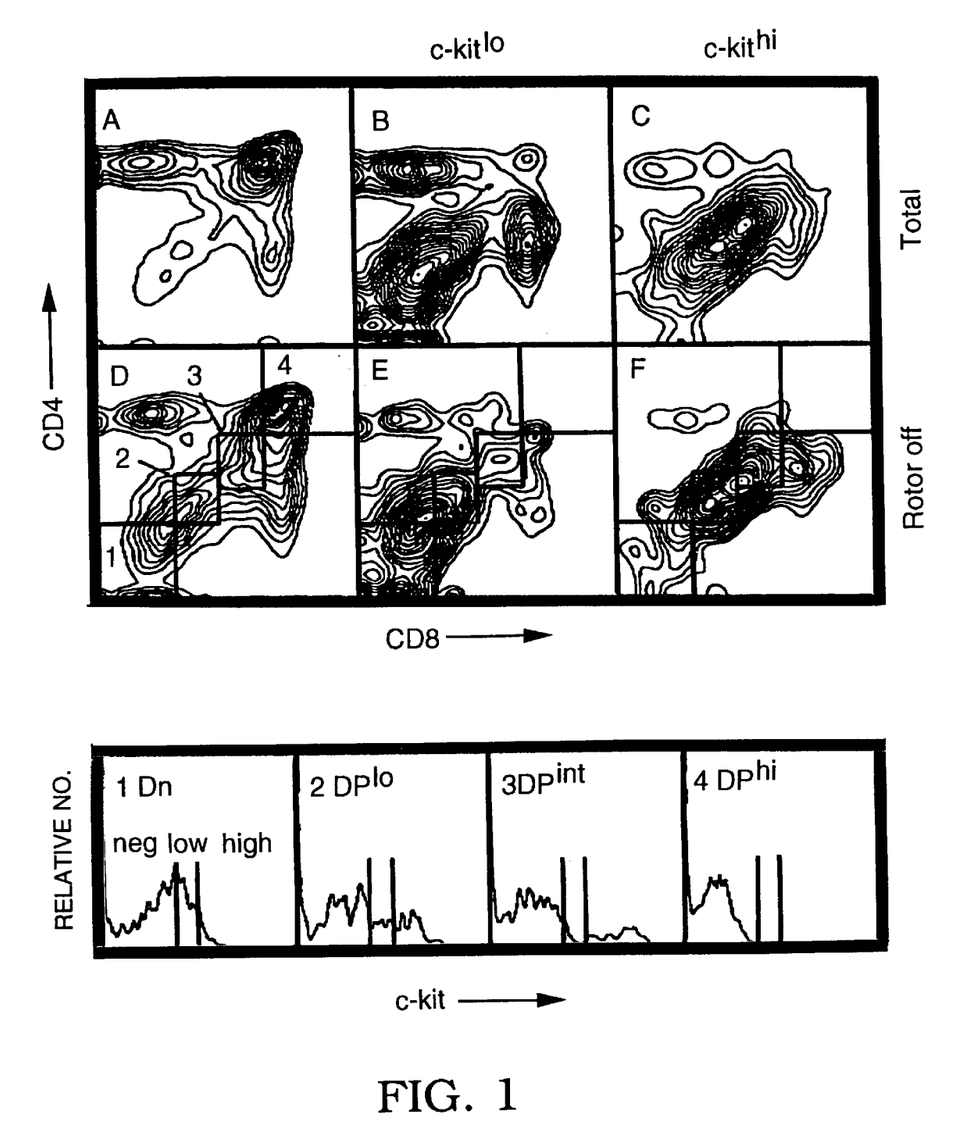
FIG. 1 shows analysis by flow cytometry of antibody staining of thymocytes, showing the CD4 and CD8 profiles of c-kit positive cells in unfractionated and blast thymocytes.

If specific selection for DP$^{int}$ or DP$^{lo}$ is desired, then the spectrum of thymocytes ranging from double negative (DN) to DP$^{hi}$ may be arranged according to intensity of staining over 4 logs of arbitrary brightness units, as illustrated in FIG. 1. The cells falling in the lowest log of brightness are designated DN, the next log are DP$^{lo}$, the next log are DP$^{int}$ and the brightest are DP$^{hi}$. Generally, the DN and DP$^{lo}$ will have a level of staining that is slightly below, or above the brightness of an isotype matched negative control, respectively.

For isolation of cells from tissue, an appropriate solution may be used to disperse the thymus. Such solution will generally be a balanced salt solution, conveniently supplemented with fetal calf serum or other naturally occurring factors, in conjunction with an acceptable buffer at low concentration, generally from 5–25 mM. Convenient buffers include HEPES, phosphate buffers, lactate buffers, etc. Otherwise thymocytes may be released from the thymus in accordance with conventional methods.

The subject cells are large, blast cells, therefore an initial separation may select for large cells by various methods known in the art, including elutriation, FICOLL-HYPAQUE™ or flow cytometry using the parameters of forward and obtuse scatter to gate for blast cells. A high proportion of the cells are in the mitotic cycle, and vital DNA stains, such as Hoechst 33842 and the like, can be used for separation.

Separation of the subject cell population will then use affinity separation to provide a substantially pure population. Techniques for affinity separation may include magnetic separation, using antibody-coated magnetic beads, affinity chromatography, cytotoxic agents joined to a monoclonal antibody or used in conjunction with a monoclonal antibody, e.g. complement and cytotoxins, and "panning" with antibody attached to a solid matrix, eg. plate, or other convenient technique. Techniques providing accurate separation include fluorescence activated cell sorters, which can have varying degrees of sophistication, such as multiple color channels, low angle and obtuse light scattering detecting channels, impedance channels, etc. The cells may be selected against dead cells by employing dyes associated with dead cells (propidium iodide, LDS). Any technique may be employed which is not unduly detrimental to the viability of the selected cells.

The affinity reagents may be specific receptors or ligands for the cell surface molecules indicated above. In addition to antibody reagents, peptide-MHC antigen and T cell receptor pairs may be used; peptide ligands and receptor; effector and receptor molecules, and the like. Antibodies and T cell receptors may be monoclonal or polyclonal, and may be produced by transgenic animals, immunized animals, immortalized human or animal B-cells, cells transfected with DNA vectors encoding the antibody or T cell receptor, etc. The details of the preparation of antibodies and their suitability for use as specific binding members are well-known to those skilled in the art.

Of particular interest is the use of antibodies as affinity reagents. Conveniently, these antibodies are conjugated with a label for use in separation. Labels include magnetic beads, which allow for direct separation, biotin, which can be removed with avidin or streptavidin bound to a support, fluorochromes, which can be used with a fluorescence activated cell sorter, or the like, to allow for ease of separation of the particular cell type. Useful fluorochromes include phycobiliproteins, e.g. phycoerythrin and allophycocyanins, fluorescein and Texas red.

The antibodies are added to a suspension of thymocytes, and incubated for a period of time sufficient to bind the available cell surface antigens. The incubation will usually be at least about 5 minutes and usually less than about 30 minutes. It is desirable to have a sufficient concentration of antibodies in the reaction mixture, so that the efficiency of the separation is not limited by lack of antibody. The appropriate concentration is determined by titration. The medium in which the cells are separated will be any medium which maintains the viability of the cells. A preferred medium is phosphate buffered saline containing from 0.1 to 0.5% BSA. Various media are commercially available and may be used according to the nature of the cells, including Dulbecco's Modified Eagle Medium (dMEM), Hank's Basic Salt Solution (HBSS), Dulbecco's phosphate buffered saline (dPBS), RPMI, Iscove's medium, PBS with 5 mM EDTA, etc., frequently supplemented with fetal calf serum, BSA, HSA, etc.

The labeled cells are then separated as to the expression of c-kit, CD4 and CD8. The first population is selected that is c-kit positive, and CD4 and CD8 intermediate to positive. Optionally the cell population is also selected for one or more of the markers: low level expression of CD3; expression of CD44; expression of CD69; expression of heat stable antigen (HSA); expression of interleukin-2 receptor a (IL-2Ra) and expression of interleukin-7 receptor (IL-7R). The second population is $DP^{lo}$ and c-kit positive.

The separated cells may be collected in any appropriate medium that maintains the viability of the cells, usually having a cushion of serum at the bottom of the collection tube. Various media are commercially available and may be used according to the nature of the cells, including DMEM, HBSS, DPBS, RPMI, Iscove's medium, etc., frequently supplemented with fetal calf serum.

Compositions highly enriched for T cell progenitor activity are achieved in this manner. The subject population will be at or about 90% or more of the cell composition, and preferably be at or about 95% or more of the cell composition. The desired cells are identified by being $c-kit^+$, $CD4^{int}$, $CD8^{int}$, $CD3^{lo}$, and being able to provide for development in vivo and in vitro of mature T cells in both the CD8+ and CD4+ lineages. The second population is identified as $DP^{lo}$ and c-kit positive. The enriched cell population may be used immediately, or may be frozen at liquid nitrogen temperatures and stored for long periods of time, being thawed and capable of being reused. The cells will usually be stored in 10% DMSO, 50% FCS, 40% RPMI 1640 medium. Once thawed, the cells may be expanded by use of growth factors or stromal cells associated with T cell proliferation and differentiation.

The subject cell population, as part of the maturation pathway, express high levels of bcl-2, while cells in the default pathway that are destined to die express lower levels. These $DP^{int}$ $c-kit^+$ cells are the object of thymic selection. Cells failing positive selection down regulate their expression of c-kit and bcl-2 as an early event, rendering them susceptible to apoptosis induced by endogenous glucocorticoids.

The enriched cell population may be grown in vitro under co-culture conditions, where thymic stromal cells are used for the co-culture, referred to as heterogeneous thymus stromal cells ("HTSC"). The thymic stromal cells can be obtained from a thymus of a particular species, at a relatively young age, or fetal, usually at an age less than about 25%, more usually less than about 15%, of the normal lifespan of the particular species. These cells will normally include various types of stromal cells (cortical and medullary types, epithelial cells, mesenchymal derivatives, dendritic cells, and macrophages), the epithelial cells being of particular importance. The cells may be dispersed in appropriate medium by any convenient means, using physical separation, enzymatic separation, e.g. collagenase, trypsin/EDTA, etc., or the like.

The nutrient medium that is employed may be any conventional medium for growing mammalian cells, such as dMEM, RPMI, MEM, Iscove's media, etc. Included in the medium will be a fibroblast growth inhibitor, conveniently an unnatural stereoisomer amino acid, particularly an aliphatic amino acid, preferably a non-polar amino acid, particularly D-valine. The D-valine will be present in from about 50 to 120 mg/L, usually about 90 mg/L. Where an unatural amino acid is present in the medium, the medium will be formulated to be deficient in the natural stereoisomer of the amino acid, e.g. L-valine free DMEM.

The stromal cells are normally grown for at least about 2 weeks, more usually for at least about 3 weeks and not more than about 10 weeks, more usually not more than about 6 weeks, prior to use with the cells of interest. In some instances, it may be desirable to remove adherent cells from the primary culture in a fixed container, using trypsin and EDTA treatment and transfer them to another container, e.g. multiwell plates.

The stromal cells may come from any convenient vertebrate, particularly mammalian, host, such as primate, including human, murine, ovine, porcine, equine, canine, feline, lagomorpha, bovine, avian, and the like, conveniently murine. In some cases, stromal cells having the same MHC type as the thymocyte cells are preferred. The stromal cells which are employed need not be the same species as the cells of interest. Stromal cells from one species may therefore be used in combination with the same or different species, e.g. murine stromal cells with human T-cell progenitors, particularly when the stromal cells are modified to express MHC genes that match the T cell recipient.

Prior to introducing the progenitor cell population, the medium will normally be exchanged, so as to remove the presence of the unnatural stereoisomer amino acid. The cell population of interest may then be added to the stromal cell culture. The cell population may be conveniently suspended in an appropriate nutrient medium, such as Iscove's modified DMEM or RPMI-1640, normally supplemented with fetal calf serum (about 5–10%), L-glutamine, a thiol, particularly 2-mercaptoethanol and antibiotics, e.g. penicillin and streptomycin. The cell population of interest may then be removed from the co-culture by any convenient means, e.g. gentle pipetting, at various times after addition. It is found that with T-cell progenitors, e.g. thymocytes, a substantial change in the cell population profile can occur within one day.

The subject co-cultures may be used in a wide variety of ways. The nutrient medium, which is a conditioned medium, may be isolated at various stages and the components analyzed. Separation can be achieved with HPLC, reversed phase-HPLC, gel electrophoresis, isoelectric focusing, dialysis, or other non-degradative techniques, which allow for separation by molecular weight, molecular volume, charge, combinations thereof, or the like. One or more of these techniques may be combined to enrich further for specific fractions.

The progenitor cells may be used in conjunction with the culture system in the isolation and evaluation of factors associated with the differentiation and maturation of T cells. Thus, the progenitor cells may be used in assays to determine the activity of media, such as conditioned media, evaluate fluids for growth factor activity, involvement with dedication of lineages, or the like.

The subject thymocyte populations may be used for reconstitution of T cell function in an immunocompromised recipient. Autologous cells, particularly if removed prior to cytoreductive or other therapy, or allogeneic cells, may be used for progenitor cell isolation. In addition, the subject cells may be modified, where DNA may be introduced by various techniques, such as spheroplast fusion, electroporation, or the like, where the cells may then be used in a variety of ways, to study various features of T-cell development, use the T-cells in various therapies, such as the treatment of cancer, infection, or the like. Genes may be introduced for a variety of purposes, e.g. prevent HIV infection, provide recognition of a particular MHC antigen-peptide complex, suppress activation of a particular T-cell TCR, etc. As these two populations are largely mitotic, they are particularly good candidates for gene introduction techniques.

Depending upon the nature of the cells, the therapy involved and the disorder, the cells are introduced into the recipient. The number of cells administered will vary widely, depending upon the particular application and the manner in which the cells are administered. Various techniques have been established for infusion of cells into a host, where the cells may be injected, introduced by catheter, infusion, etc. Where the subject cells are directly introduced into a recipient with further differentiation or expansion, it is preferable to inject the cells into the thymus of the recipient.

The T cell progenitors may be used for the treatment of genetic diseases. Genetic diseases associated with T cells may be treated by genetic modification of autologous or allogeneic progenitor cells to correct a genetic defect or treat to protect against disease, e.g. HIV. For example, diseases such as adenosine deaminase deficiency, recombinase deficiency, recombinase regulatory gene deficiency, etc. may be corrected by introduction of the wild-type gene into the progenitor cell, either by homologous or random recombination. Particular T cell receptor gene combinations can be introduced to provide an amplified population of T cells responsive to recipient MHC in conjunction with foreign peptide, for example, anti-HLA-A2 restricted HIV peptides. Alternatively, normal allogeneic progenitor cells may be transplanted. Other methods of gene therapy are the introduction of drug resistance genes to enable normal progenitor cells to have an advantage and be subject to selective pressure, e.g. the multiple drug resistance gene (MDR).

Various vectors may be employed for insertion of exogenous genes. In most cases a retroviral vector will be used, with combinations of retroviruses and an appropriate packaging line where the capsid proteins will be functional for infecting human cells. Various amphotropic virus-producing cell lines are known, such as PA12 (Miller et al., *Mol. Cell. Biol.* 5 (1985), 431–437), PA317 (Miller et al., *Mol. Cell. Biol.* 6 (1986), 2895–2902) GRIP (Danos et al., PNAS 85 (1988), 6460–6464). Of particular interest in the kat system for transduction of primary human T lymphocytes (Finer et al. (1994) Blood 83:43–50). Usually, the cells and virus will be incubated for at least about 24 hours in the culture medium. The cells are then allowed to grow in the culture medium for at least about two weeks, and may be allowed to grow for at least about five weeks or more, before transplantation.

The constructs which will be employed will normally include a marker, which allows for selection of cells into which the DNA has been integrated, as against cells which have not integrated the DNA construct. Various markers exist, particularly antibiotic resistance markers, such as resistance to G418, hygromycin, and the like. Less conveniently, negative selection may be used, where the marker is the HSV-tk gene, which will make the cells sensitive to agents, such as acyclovir and gancyclovir.

The constructs can be prepared in a variety of conventional ways. Numerous vectors are now available which provide for the desired features, such as long terminal repeats, marker genes, and restriction sites. One may introduce the vector in an appropriate plasmid and manipulate the vector by restriction, insertion of the desired gene with appropriate transcriptional and translational initiation and termination regions, and then introduce the plasmid into an appropriate packaging host. At each of the manipulations, one may grow the plasmid in an appropriate prokaryotic host, analyze the construct to ensure that the desired construct has been obtained, and then subject the construct to further manipulation. When completed, the plasmid or excised virus may then be introduced into the packaging host for packaging and isolation of virus particles for use in the genetic modification.

The following examples are offered by way of illustration and not by way of limitation.

EXPERIMENTAL

Experimental Procedures

Mice

Four to six weeks old C57BL6/Ka (LY5.1; Thy 1.2), C57BL6 (Ly5.2; Thy1 1.2) and C57BL/Ka Thy1.1 (Ly5.1; Thy1.1) mice were bred and maintained in the central animal facility in the Department of Comparative Medicine, Stanford University.

Antibodies

The antibodies used in immunofluorescence staining included 19XE5 (anti-Thy1.1); AL1-4A2 (anti-Ly5.1); 2B8 (anti-c-kit, CD117, Ikuta and Weissman, supra.); E-13 161–7 (anti-sca-1); E-3 81–2 (anti-sca-2); KT-31 (anti-CD3); GK-1.5 (anti-CD4); 53-6.7 (anti-CD8); 6B2 (anti-B220), M1/70 (anti-Mac-1) and 8C5 (anti-Gr-1). Mouse and hamster antibodies, e.g. 19XE5 were purified by protein A affinity chromatography, and rat antibodies, e.g. 6B2, M1/70, were purified by protein G affinity chromatography. GK-1.5 and 53-6.7 were always conjugated with phycoerythrin (PE) (Cyanotech Corporation, Kailua-Kona, Hawaii) and fluorescein-5-isothiocyanate (FITC) (Molecular Probes, Incorporated, Eugene, Ore.), respectively. 2B8 and AL1-4A2 were conjugated with allophycocyanin (APC) (Cyanotech Corporation). The other antibodies were biotinylated. Biotinylated anti-IL-7R Mab (Sudo et al. (1993) *Proc. Natl. Acad. Sci.* 90:9125–9129) was a gift from Dr. Shin-Ichi Nishikawa (Kyoto University, Kyoto, Japan). Biotinylated M1/69 (anti-heat stable antigen), 7D4 (anti-IL-2Ra), IM7 (anti-CD44) and GL3 (anti-TcR-γ/δ), and FITC-conjugated CD69 (H1.2F3) were purchased from PharMingen (San Diego, Calif.). They were visualized with avidin-Texas red (Becton Dickinson & Co., San Jose, Calif.).

Size Fractionation of Thymocytes by Centrifugal Elutriation

Single cell suspensions of thymocytes were obtained from thymus from 5 to 8 mice (4 to 6 weeks old), by passing through a stainless mesh followed by a 70 μm nylon cell strainer (Falcon 2350; Becton Dickinson Labware, Franklin Lakes, N.J.). They were resuspended at $1 \times 10^8$ cells/ml in phosphate buffer saline containing 0.5% bovine albumin (PBS/BSA). Ten ml of these cells were loaded into a J2-21M elutriator with a JE6B rotor (Beckman Instruments, Palo Alto, Calif.) spinning at 3000 rpm at 4° C. The cells were elutriated with continuous flow of (PBS/BSA) into 200 ml fractions. The loading flow-through fraction was collected at 16 ml/min, and contained erythrocytes and dead cells. Thymocytes were divided into four fractions: 16–20 ml/min, 21–24 ml/min, 25–28 ml/min and rotor off populations.

Cell Sorting and Flow Cytometric Analysis

Freshly isolated thymocytes or blast thymocyres obtained by elutriation described above were stained for multi-color analysis, and the fluorescence was analyzed using a highly modified dual (488-nm argon laser and 599-nm dye laser) or triple laser (plus 390-nm argon laser) FACS (Becton Dickinson Immunocytometry Systems, Mountain View, Calif.) with four-decade logarithmic amplifiers as described in Parks and Herzenberg (1984) *Meth. Enzymol.* 108:197–241. B-cell, monocytes and granulocytes appeared as a minority in the 21–28 mil/min elutriator fraction and were virtually depleted in the rotor off (blast) population as detected by five-color staining with biotynylated B-220, Mac-1 and Gr-1, followed by avidin-Texas red (IR) in addition to CD4-PE, CD8-FITC, c-kit-APC and propidium iodide (PI) by using triple-laser FACS. The major population of other lineages (<0.01% of freshly-isolated thymocytes) were c-kit negative. Usually, dead cells were detected by adding 1 μg/ml of propidium iodide (PI), and gated out by setting an electronic gate to exclude PI-positive cells. In some cases, dead cells were eliminated by scatter gating. Contaminating stromal cells present in thymocyte populations were also eliminated by setting electronic gates on forward angle light scatter as well as on obtuse scatter (granularity measuring index). In evaluating the distribution of c-kit+ thymocytes, the thymocytes were first sorted with electronic gates on forward angle light scatter and obtuse scatter before analysis to eliminate or break doublets of thymocytes. The sorted cells were then reanalyzed. Usually, the data of more than 50,000 c-kit+ thymocytes were collected for this purpose. Fluorescence data were analyzed by FACS/DESK program, and presented either in the form of histograms or two-parameter probability plots (5%).

FACS Analysis for bcl-2

The staining of bcl-2 was done according to the modified method described in Veis et al. (1993) *J. Immunol.* 151:2546–2554. Briefly, cells were stained with FITC-CD8, biotinylated-CD4 and c-kit- APC, followed by avidin-Texas Red. The cells were fixed with 2% paraformaldehyde for 5 min at 4° C. The cells were washed and treated with 0.3% saponin for 10 min in room temperature. After this fixation procedure, the cells were stained with purified hamster anti-mouse bcl-2 antibody (PharMingen), followed by PE-conjugated Goat anti-hamster IgG (Caltag Laboratories, San Francisco, Calif.); using a staining media of PBS containing 0.03% saponin. They were analyzed by a dual laser FACS.

Cell Cycle Analysis

The FACS sorted cells (usually 50,000 cells) were suspended with 500 μl of distilled water containing 0.1% of Triton-X 100, 50 μg/ml of PI, and 0.1% of sodium citrate. After overnight on ice, they were analyzed by a dual laser FACS.

HTSC Culture System

Thymic stroma cells from 4–6-wk-old C57BL6/Ka or C57BL/Ka Thy 1.1 mice were cultured as described previously in detail (Sen-Majumdar et al. (1992) *J. Exp. Med.* 176:543–551). Briefly, after removing the thymocytes by passing through a stainless mesh, stromal cells were grown in valine free-MEM containing D-valine for 2–3 weeks. Then, the adherent cells from primary culture dishes were removed by trypsin-EDTA treatment, and placed into 24-well (Costar, Cambridge Mass.) plates. D-valine containing medium was withdrawn just before sorted thymocytes were added to the epithelial cultures. Sorted thymocytes (usually $2-4\times10^4$ cells) were resuspended in RPMI-1640 supplemented with 10% FCS, L-glutamine, and penicillin-streptomycin. After the culture, thymocytes were removed by gentle pipetting. The harvested cells were stained with CD4-PE, CD8-FITC, PI and/or biotinylated CD3, followed by avidin-Texas-red. Contamination of stromal cells and dead cells was avoided by setting a strict electronic gate of forward angle light scatter and obtuse scatter and by PI staining. Recovery rates were around 20–30% of c-kit+ cells after 12–16 h culture. Polyclonal rabbit neutralizing anti-mouse Slf, and monoclonal rat neutralizing anti-mouse c-kit (ACK-2) were purchased from Genzyme (Cambridge, Mass.), and GIBCO BRL (Gaitherburg, Md.), respectively. Titration of these antibodies was done by using a murine Slf-and IL-7- dependent cell line (Domen et al. (1993) *J. Exp. Med.* 178:1665–1673.). One μg of the antibody could neutralize 1 ng/ml of recombinat rat Slf. In inhibition analyses, stromal cells S were incubated with 500 μl of RPMI-1640 containing 10% FCS and 1 μl of anti-mouse Slf, and FACS sorted c-kit+ thymocytes were incubated with 500 μof RPMI-1640 containing 10% FCS and 1 μg/ml of ACK-2 for 30 min before the start of cultures. Recombinant rat Slf (provided by Amgen, Inc.) was used at 1 ng/ml.

Apoptosis Staining after in vivo Treatment with Corticosteroid

C57BL/6J mice (4 weeks old) were treated with different doses of dexamethasone (i.p.). Sequential analysis of thymocyte number after injection of dexamethasone revealed that total thymocyte number had not decreased 6 h after injection, but significantly decreased after 24 h , probably due to rapid phagocytosis by thymic macrophages. Accordingly, apoptotic thymocytes were evaluated 6 h after injection. Apoptosis staining was performed by a method reported previously (Cohn et al. (1993) *J. Immunol.* 151:566–574) with slight modification. Cells were first stained for CD4, CD8, and c-kit. The cells were incubated with the vital bisbenzimidazole dye, Hoechst 33342 (1

μg/ml) for 10 min on ice, followed by addition of PI (1 μg/ml). Flow cytometric analysis was performed using three laser FACS. Dead cells were removed as PI-positive cells. The remaining cells were devided into Hoechst$^{hi}$ and Hoechst$^{lo}$ populations; the former are apoptotic and the latter are non-apoptotic cells. Only the DNA from Hoechst$^{hi}$ population gave degradation into oligonucleosomal fragments by the method described by Smith et al. (1989) *Nature* 336:73–76.

Intrathymic Injection

The details of the surgical procudure have been described elsewhere (Guidos et al. (1990) *J. Exp. Med.* 172:835–845). One to 1.5×10$^5$ of c-kit$^{hi}$ CD4+8+ blast thymocytes (DP$^{int}$) isolated from C57BL/Ka Thy 1.1 (Ly5.1;Thy1.1) mice by elutriation and cell sorting in 10 μl of saline were injected into a thymic lobe of anesthetized, unirradiated 3–5-wk-old C57BL6 Ly5.2 (Ly5.2; Thy1.2) mouse. Three or four days later, thymocyte suspensions made from individual thymic lobes were stained with biotinylated anti-Thy 1.2 antibodies. Cells were washed and resuspended in 1 ml staining medium plus 200 ul avidin-conjugated paramagnetic beads (Advanced Magnetics, Inc., Cambridge, Mass.). After 30 min at 4° C. with constant mixing, cell-bead complexes were removed from free cells using a magnetic separator (BioMag; Advanced Magnetics, Inc., Cambridge, Mass.). The free cells were stained with avidin-Texas red, PE-GK1.5, FITC-56.6.8 and APC-Ly 5.1. The donor cells were seen as the Texas red-negative, APC-positive population. All data of donor cells (usually 3 to 5×10$^3$ cells) was collected by setting electronic gates.

Results c-kit Expression in Thymocytes Reveals New Subpopulations

Thymocytes were subfractionated into four different elutriator fractions. The small cells obtained with a flow rate fraction of 16 to 20 ml/min were mostly CD4$^+$8$^+$ thymocytes. Most of the CD4$^+$8$^-$ or CD4$^-$8$^+$ single positive (SP) thymocytes, and CD4$^+$8$^{lo}$ or CD4$^{lo}$8$^+$ transitional thymocytes appeared in the small to medium-sized thymocyte population (21 to 28 ml/min). In the rotor off population (around 10% of total thymocytes), containing blast thymocytes, most SP thymocytes and CD4$^+$8$^{lo}$ or CD4$^{lo}$8$^+$ transitional thymocytes were depleted. The majority of the blast population consisted of CD4$^-$8$^-$ and CD4$^+$8$^+$ thymocytes. Table 1 shows the percentages of c-kit+ cells in each elutriator fraction, c-kit+ cells were highly enriched (up to 9%) in the blast population, and were virtually absent from the small cell enriched elutriator (16 to 24 ml/min) fractions, that include around 70% of all thymocytes. Cycling cells were mostly seen in blast thymocyte populations, indicating that only the blast populations are responsible for expanding thymocyte populations (Table 1 and 2).

B-cells, monocytes and granulocytes appeared as a minority of cells (<0.05%) in the 21–28 ml/min elutriator fraction. These cells were c-kit negative.

FIG. 1 shows the distribution of c-kit+ cells in the whole and the blast thymocyte populations. In previous studies, arbitrary lines were drawn between double negative (DN:CD4$^-$8$^-$) and double positive (DP:CD4$^+$8$^+$) stages. To evaluate the c-kit distribution precisely, we divided CD4$^+$8$^+$ thymocytes into DP low (DP$^{lo}$), DP intermediate (DP$^{int}$) and DP high (DP$^{hi}$) subpopulations (FIG. 1D). In most previous reports, CD4$^-$8$^-$ (DN) thymocytes were included in the fractions here called DN plus DP$^{lo}$ thymocytes, while CD4$^+$8$^+$ (DP) thymocytes were in the DP$^{int}$ plus DP$^{hi}$ fractions.

In unfractionated thymocytes, c-kit+ cells were seen in several CD4$^-$ and CD8$^-$ defined subpopulations, including DN, DP$^{lo}$, DP$^{int}$, and CD4$^+$8$^{lo}$ and CD4$^{lo}$8$^+$ transitional thymocytes; DP$^{hi}$ thymocytes were c-kit-. The c-kit+ cells can be arbitrarily divided into c-kit$^{lo}$ and c-kit$^{hi}$ subsets (FIG. 1). c-kit$^{hi}$ thymocytes were mainly seen in the DP$^{lo}$ and DP$^{int}$ subsets, whereas c-kit$^{lo}$ cells were mostly present in DN and CD4$^+$8$^{lo}$ or CD4$^{lo}$8+ transitional thymocytes. The distribution of c-kit$^+$ cells were similar in thymic blasts; >80% of c-kit$^{hi}$ cells were included in the rotor off population (Table 1), while most of c-kit$^{lo}$ transitional thymocytes (CD4+8$^{lo}$ or CD4$^{lo}$8+) were smaller, and not included in the rotor off fraction (FIGS. 2E and F). c-kit profiles in each differentiation stage of thymic blasts (the bottom panels of FIG. 1) indicated that c-kit$^{hi}$ cells are found as a distinct population in the DP$^{int}$ stage.

TABLE 1

Percentages of c-kit- Positive Cells and Cycling Cells in Elutriator Fraction

| Flow Rate (ml/min) | Total % of Cells | % c-kit$^{lo}$ of Fraction (of Total) | % c-kit$^{hi}$ of Fraction (of Total) | % of Cycling Cells |
|---|---|---|---|---|
| 16–20 | 9.5 | 0.02 (<0.01) | <0.01 (<0.01) | 0 |
| 21–24 | 60.4 | 0.30 (0.18) | 0.04 (0.02) | 0.8 |
| 25–28 | 17.8 | 1.45 (0.26) | 0.27 (0.05) | 3.1 |
| Rotor Off | 12.2 | 6.22 (0.76) | 2.74 (0.34) | 33.2 |

Total thymocytes were subfractionated according to different flow rates (ml/min) on elutriation. Parenthesis indicate estimated percentages of c-kit-positive cells in total thymocytes. Cycling cells represent cells in S/G$_2$/M phases of cell cycle of PI staining as described in Experimental Procedure. Results are shown in mean values of three independent experiments.

In both total and blast thymocyte populations, c-kit+ cells could be seen in DP$^{lo}$, DP$^{int}$ and either CD4$^+$8$^{lo}$ or CD4$^{lo}$8$^+$ transitional thymocytes, but not in DP$^{hi}$ thymocytes. The distribution of c-kit$^+$ cells from DN to DP$^{int}$ stages was slightly skewed toward CD8 (FIG. 1). The data suggest that some fraction of CD4$^+$8$^{lo}$ or CD4$^{lo}$8+ transitional thymocytes directly differentiate from the DP$^{int}$ c-kit$^{hi}$ subset of DP thymocytes, and not from the more numerous DP$^{hi}$ thymic blast cell populations. Therefore, the differentiation potential of DP$^{int}$ c-kit$^{hi}$ blast thymocytes was further characterized.

Figure 2:
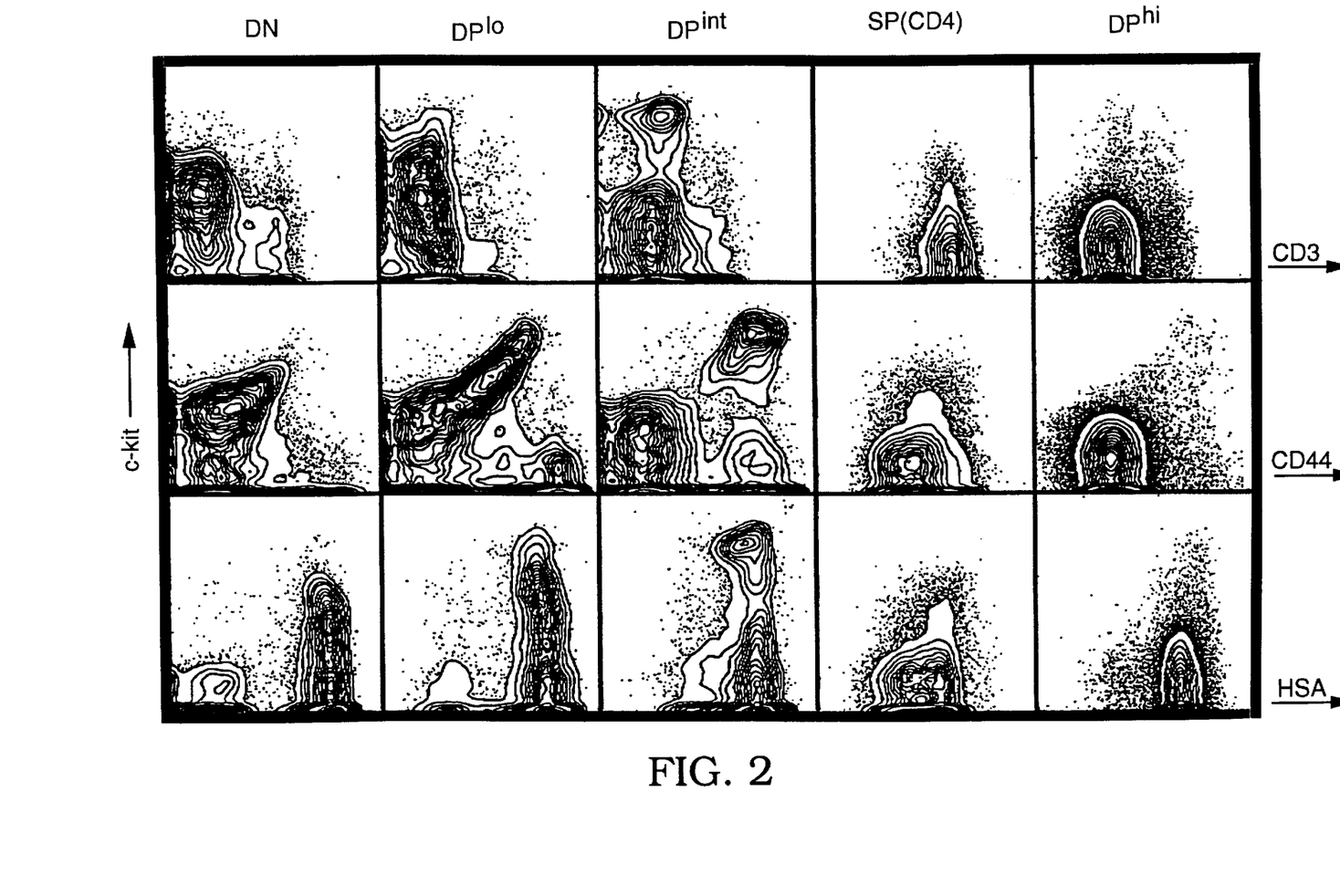
FIG. 2 shows the phenotypic characterization of thymocyte subpopulations with respect to expression of CD3, CD44, HSA and c-kit.

The DP$^{int}$ c-kit$^{hi}$ Population Phenotypically are CD3$^{lo}$, CD44$^{hi}$, HSA$^{hi}$, and Express IL-2 and IL-7 receptors FIG. 2 shows the phenotypic characteristics of c-kit$^+$ cells in several differentiation stages of blast thymocyte subpopulations. Around 40% of DN blast thymocytes were c-kit$^{lo}$. The DP$^{int}$ cells, however, contained a distinct subset of c-kit$^{hi}$ cells (around 15% of DP$^{int}$ thymic blasts). These c-kit$^{hi}$ cells expressed low levels of CD3, and were strongly positive for CD44 and heat stable antigen (HSA). The DP$^{int}$ c-kit$^{hi}$ thymocytes comprise only 0.2–0.3% of total thymocytes. In the DP$^{hi}$ population, we could observe some c-kit$^{hi}$ cells; however, they were only <0.01% of DP$^{hi}$ blast thymocytes. The DP$^{int}$ c-kit$^{hi}$ thymic blasts were positive for Sca-1 and Sca-2, and were negative for TcR-γ/δ. Other lineage-associated antigens such as Mac-1, Gr-1 and B220 were negative.

Figure 3:
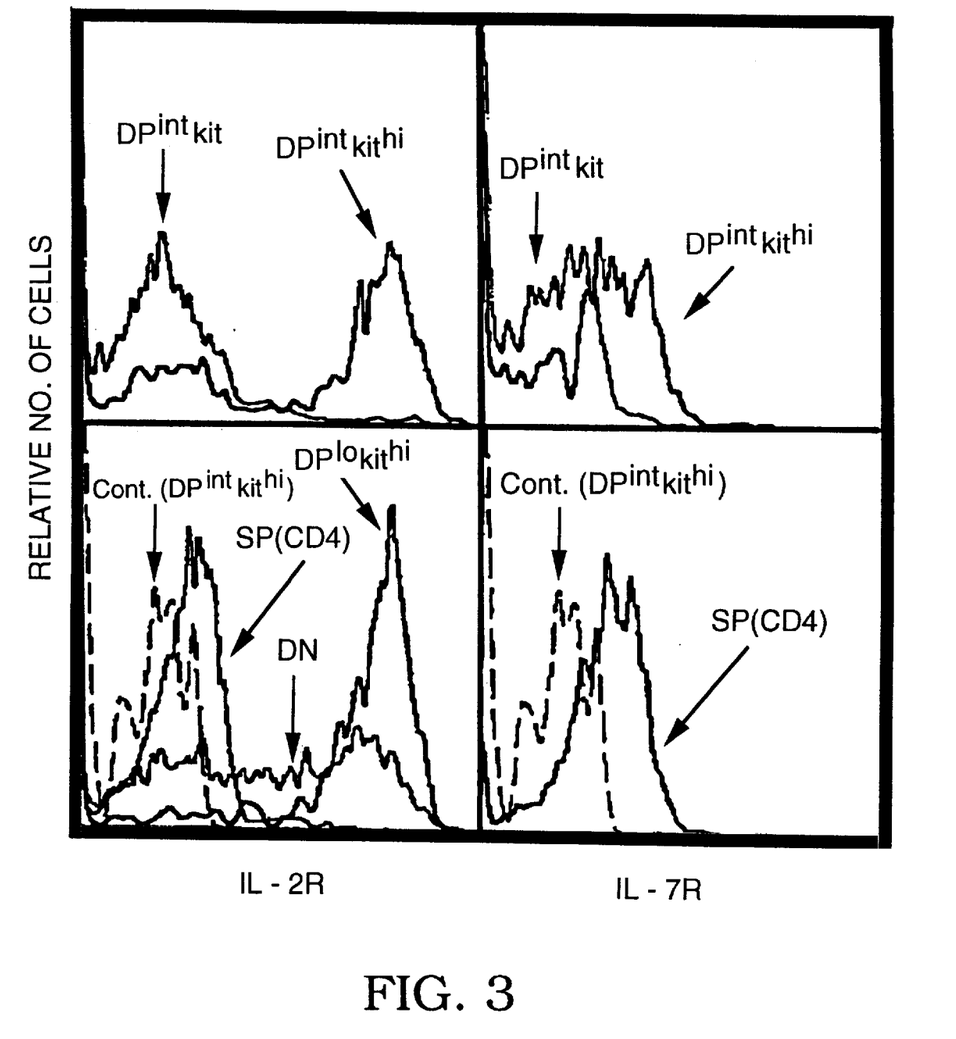
FIG. 3 shows the phenotypic characterization of thymocyte subpopulations with respect to expression of IL-2 receptor and IL-7 receptor.

FIG. 3 shows the flow cytometeric analysis of IL-7 receptor (IL-7R) and IL-2 receptor (CD25, IL-2Ra) in blast thymocytes. DN cells expressed various levels of IL-2Ra and IL-7R. In the DP$^{lo}$ stage, c-kit$^{hi}$ cells expressed both IL-7R and IL-2Ra. DP$^{int}$ c-kit$^{hi}$ cells expressed high levels of IL-7R, the expression of which was maintained in SP cells. $DP^{int}$ c-kit$^{hi}$ cells had begun to down regulate IL-2Ra; IL-2Ra was negative in c-kit$^{lo}$ transitional intermediates (CD4$^+$8$^{lo}$ and CD4$^{lo}$8$^+$), and SP cells. In contrast, most c-kit– $DP^{int}$ blasts were negative for both cytokine receptors.

Figure 4A:
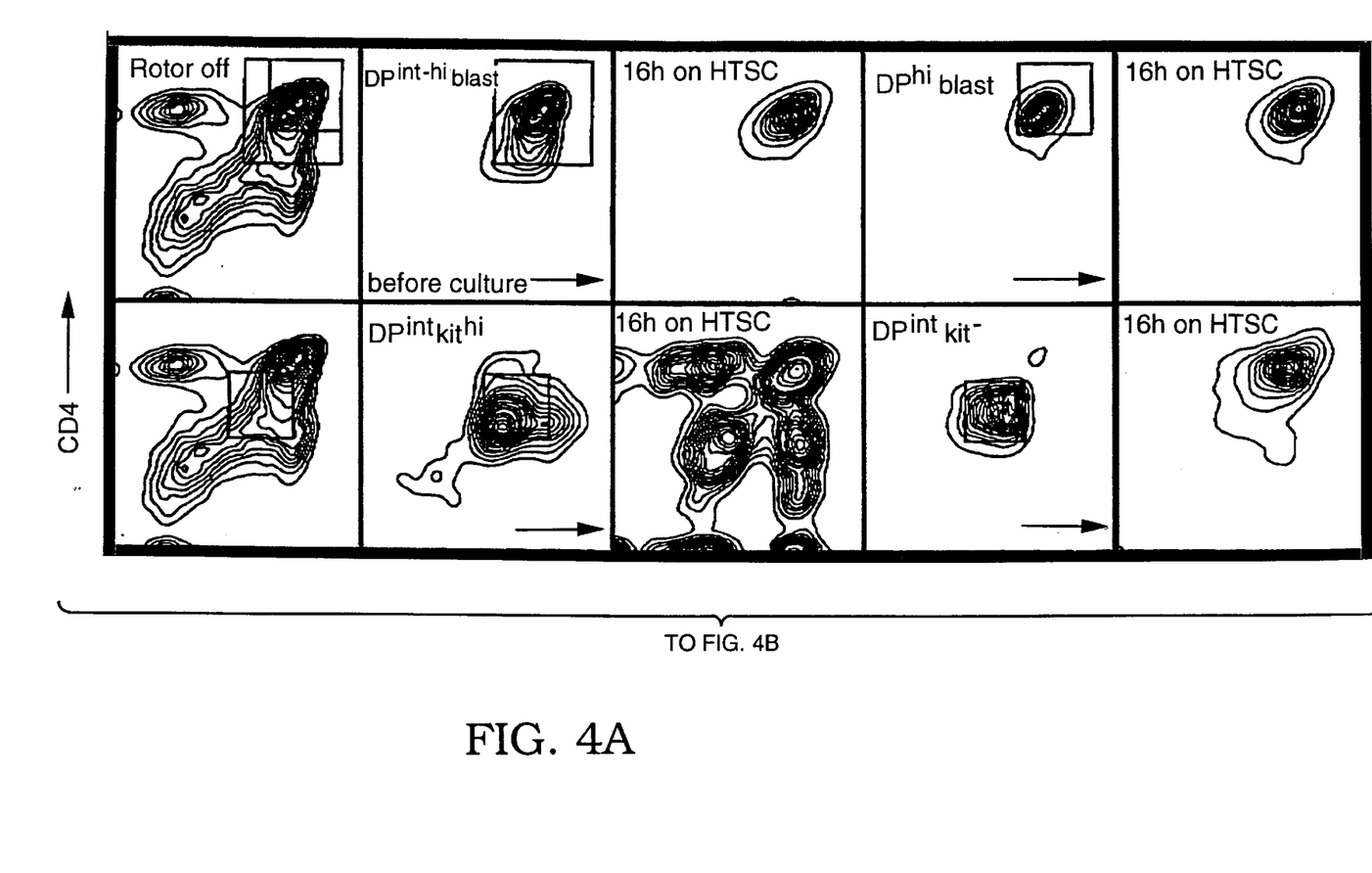
FIGS. 4A to 4B show the phenotype of $DP^{int}$ c-kit$^+$ thymocytes after culture on heterogeneous thymic stromal cells.

Differentiation Capacity of $DP^{int\ c\text{-}kit\ hi}$ Cells on Heterogenous Thymic Stroma Cell (HTSC) Cultures in vitro To evaluate the differentiational potential of $DP^{int}$ c-kit$^{hi}$ blasts in vitro, we employed the HTSC culture system. FIG. 4 shows results of short-term culture of several thymocyte subsets on HTSC. At first, all $DP^{int}$ and $DP^{hi}$ blasts were cultured, but no differentiation of SP cells from this pool was detectable (FIG. 4A), even after 36 h cultivation. $DP^{hi}$ blasts (FIG. 4A) and $DP^{hi}$ thymocytes sorted from any other elutriator fraction (FIG. 4C: 25–28 ml/min) also did not differentiate to SP cells. Because phenotypic analysis showed the CD4 and CD8 maturation pathways to be composed of c-kit$^+$ cells, and of the DP blast, only the $DP^{int}$ cells were c-kit$^+$, the $DP^{int}$ subsets were examined for their maturation potential.

$DP^{int}$ blasts were subdivided into c-kit$^+$ and c-kit– populations, and sorted into each population by using three color (CD4, CD8, c-kit) FACS. $DP^{int}$ c-kit$^{hi}$ blasts were large-sized cells, and expressed low levels of CD3. $DP^{int}$ c-kit– blasts were CD3$^{neg\text{-}lo}$. Both $DP^{int}$ c-kit$^{hi}$ and $DP^{int}$ c-kit– blasts were mainly in cell cycle; and around 30% of these cells were S, $G_2$ plus M phases by PI staining (Table 2).

TABLE 2

Cell cycle Status of Sorted Thymocyte Subpopulations

| | % of Cells in S/G$_2$/M Phases | | | |
|---|---|---|---|---|
| Flow Rate | DN | DP$^{lo}$ | DP$^{int}$ | DP$^{hi}$ |
| 25–28 | ND | ND | <0.1 | 3.5 |
| Rotor Off | 24.9 | 32.3 | 33.0 | 29.1 |
| c-kit$^{hi}$ | ND | 31.8 | 30.0 | ND |
| c-kit$^{neg}$ | ND | 34.7 | 33.0 | ND |
| Total | 10.6 | 4.4 | 3.8 | 3.4 |

Cells in S/G$_2$/M phases of cell cycle were determined by hypotonic PI staining as described in Experimental Procedure. The definition of DN, DP$^{lo}$, DP$^{int}$ and DP$^{hi}$ are shown in FIG. 1. Total: Unfractionated Thymocytes; ND: not done.

When the sorted $DP^{int}$ c-kit$^{hi}$ and $DP^{int}$ c-kit– blasts were placed on syngeneic HTSC, they immediately attached to the stromal layer. As shown in FIG. 4, the c-kit$^{hi}$ $DP^{int}$ blast population differentiated into SP cells within 12–16 h on HTSC in three independent experiments. Their differentiation was completed within 12 h, since their profiles after 36 h culture were almost the same as those after 12 h culture (FIG. 4C). The SP cells that had differentiated from $DP^{int}$ c-kit$^{hi}$ thymocytes expressed high levels of CD3 and by forward scatter were, like SP CD3$^+$ cells in situ, medium sized cells, indicating that they had fully matured. In contrast, $DP^{int}$ c-kit– blasts differentiated into $DP^{hi}$ cells within 16 h (FIG. 4A), and showed no further differentiation, even after 36 h.

In addition to SP cells, $DP^{int}$ c-kit$^{hi}$ thymocytes produced $DP^{hi}$ and DN populations. The forward scatter profiles of these cell populations revealed that the DN progeny were very small cells, and their expression of CD3 was negative to low. The data suggests that the $DP^{hi}$ and DN were apoptotic or dying.

Figure 4B:
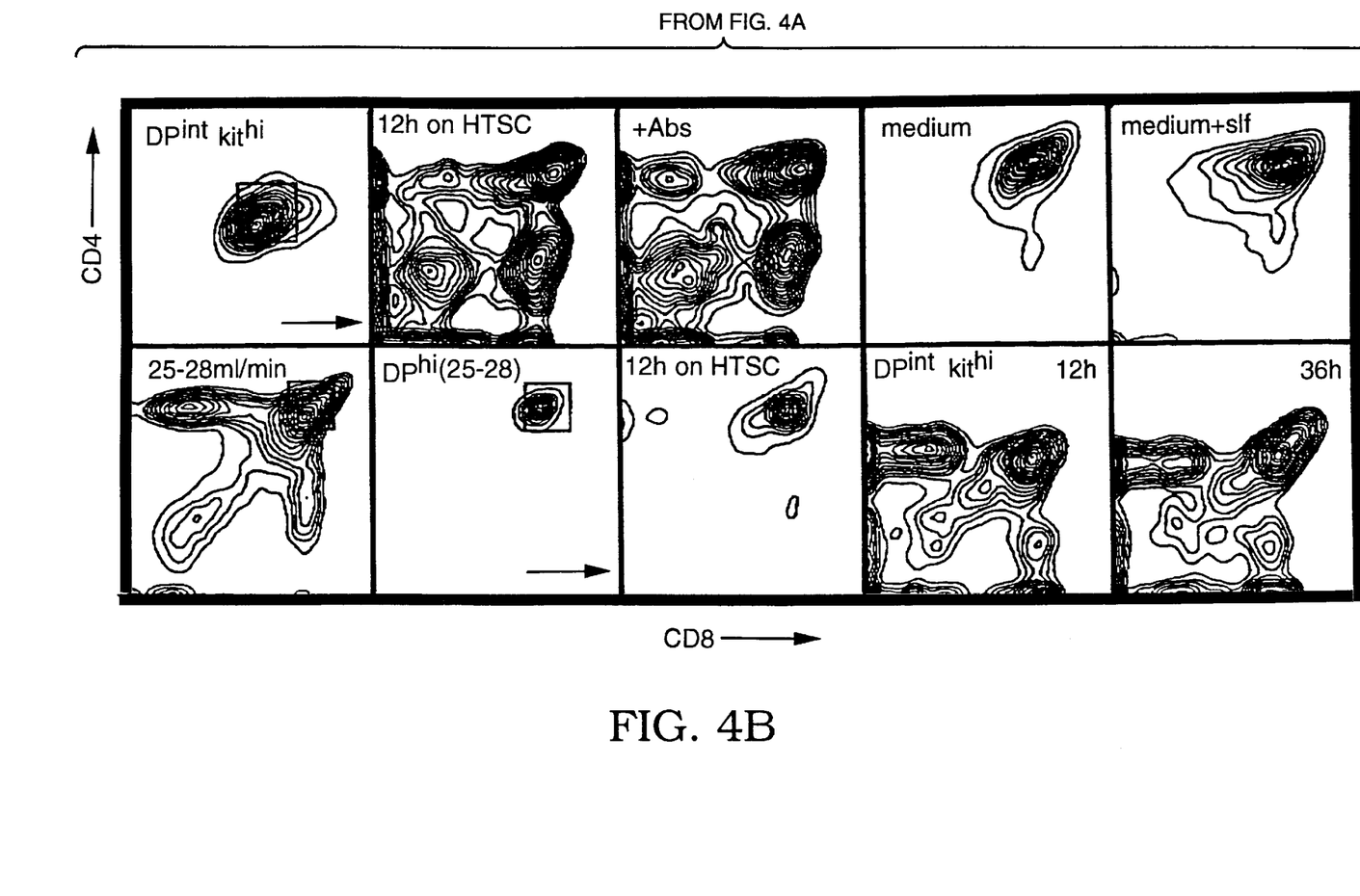

The differentiation of $DP^{int}$ c-kit$^{hi}$ thymocytes along the maturation pathway was completely dependent on the HTSC, because they could not become SP cells when cultured with the medium in the absence of the stromal layer (FIG. 4B). On the other hand, the differentiation of $DP^{int}$ c-kit– cells to $DP^{hi}$ cells occurred after 12 h culture with medium only.

The addition of recombinant Slf to the medium did not promote the differentiation of $DP^{int}$ c-kit$^{hi}$ cells. Preincubation with neutralizing anti-c-kit and anti-Slf antibodies with the $DP^{int}$ c-kit$^{hi}$ thymocytes and the stromal layer, respectively, did not inhibit their differentiation (FIG. 4B). Thus, triggering c-kit in these cells is neither necessary nor sufficient for their passage along the maturation pathway, at least in vitro.

c-kit$^{hi}$ transitional intermediates were sorted and tested for their differentiation capacity on HTSC in vitro. Each population almost exclusively differentiated into either CD4$^+$8– or CD4–8$^+$ SP thymocytes after 16 h culture. They also produced $DP^{hi}$ and DN progeny in addition to SP cells. The DN progeny were again very small cells. These results indicate that c-kit$^{hi}$ CD4$^+$8$^{med}$ or CD4$^{med}$8$^+$ transitional blasts contain a major subpopulation that have committed to either the CD4 or the CD8 lineage. It is unclear that at this point if the small, $DP^{hi}$ or DN cells represent further selection, or represent those cells that have failed to interact with appropriate thymic stromal cells.

Down Regulation of c-kit after Acquisition of High Level of CD3

To study the possible progeny of $DP^{int}$ c-kit$^{hi}$ cells in greater detail, the CD3 and c-kit expression of CD4$^+$8$^{med}$ or CD4$^{med}$8$^+$ transitional intermediates was analyzed. The c-kit$^+$ transitional intermediates contained three distinct subsets: CD3$^{med}$ c-kit$^{hi}$ large to medium size cells, CD3$^{hi}$ c-kit$^{lo}$ medium-sized cells, and CD3$^{-/lo}$ c-kit$^{lo}$ small cells. The expression of CD3 in these population was not a continuum; individual cells express quantal levels of CD3. Most of the c-kit– CD3$^{-/lo}$ population were probably destined to die, because they had shrunk in size on reanalysis. Cell cycle analysis of these populations revealed that the c-kit$^{hi}$ CD3$^{med}$ cells were still dividing (around 25% were in S/G$_2$/M stages of cell cycle), while the c-kit$^{lo}$ CD3$^{hi}$ cells had largely ceased cell division.

The majority of large cells reside in the c-kit– pool, these c-kit– cells are on the default pathway, and not on the maturation pathway. The c-kit– CD3$^{-/lo}$ thymocytes were mostly $DP^{hi}$ cells without transitional intermediates. A minority of the cells were c-kit$^+$. In the c-kit$^+$ subsets, the increase of CD3 expression was associated with that of CD4 and CD8 expression: the c-kit$^{lo}$ cells are DN and $DP^{lo}$, and the c-kit$^{hi}$ CD3$^{lo}$ cells are $DP^{int}$, c-kit was gradually down regulated with up regulation of CD3 in the transitional intermediates (CD3$^{med}$CD4$^+$ CD8$^{med}$ or CD3$^{med}$ CD4$^{med}$CD8$^+$). These data are interpreted to suggest that CD3$^{hi}$ SPs are derived through the c-kit-positive pathway, and that this pathway does not include the $DP^{hi}$ stage.

The quantal stages defined by CD3 and c-kit expression are likely to be related to default, positive and negative selection events in the thymus. Their expression of the very early activation antigen was analyzed. CD69, reportedly marks thymocytes undergoing positive selection. $DP^{hi}$ (medium to large) cells (CD3$^{-/lo}$ c-kit–) as well as $DP^{lo}$ cells (CD3$^{-/lo}$ c-kit$^{lo}$) were negative for CD69. $DP^{int}$ c-kit$^{hi}$ (CD3$^{lo}$) cells were weakly positive for CD69, and gradual increases of CD69 were seen in CD3$^{med}$ c-kit$^{hi}$ and CD3$^{hi}$ c-kit$^{lo}$ cells.

Differentiation Capacity of $DP^{int}$ c-kit$^{hi}$ Cells in vivo

Figure 5:
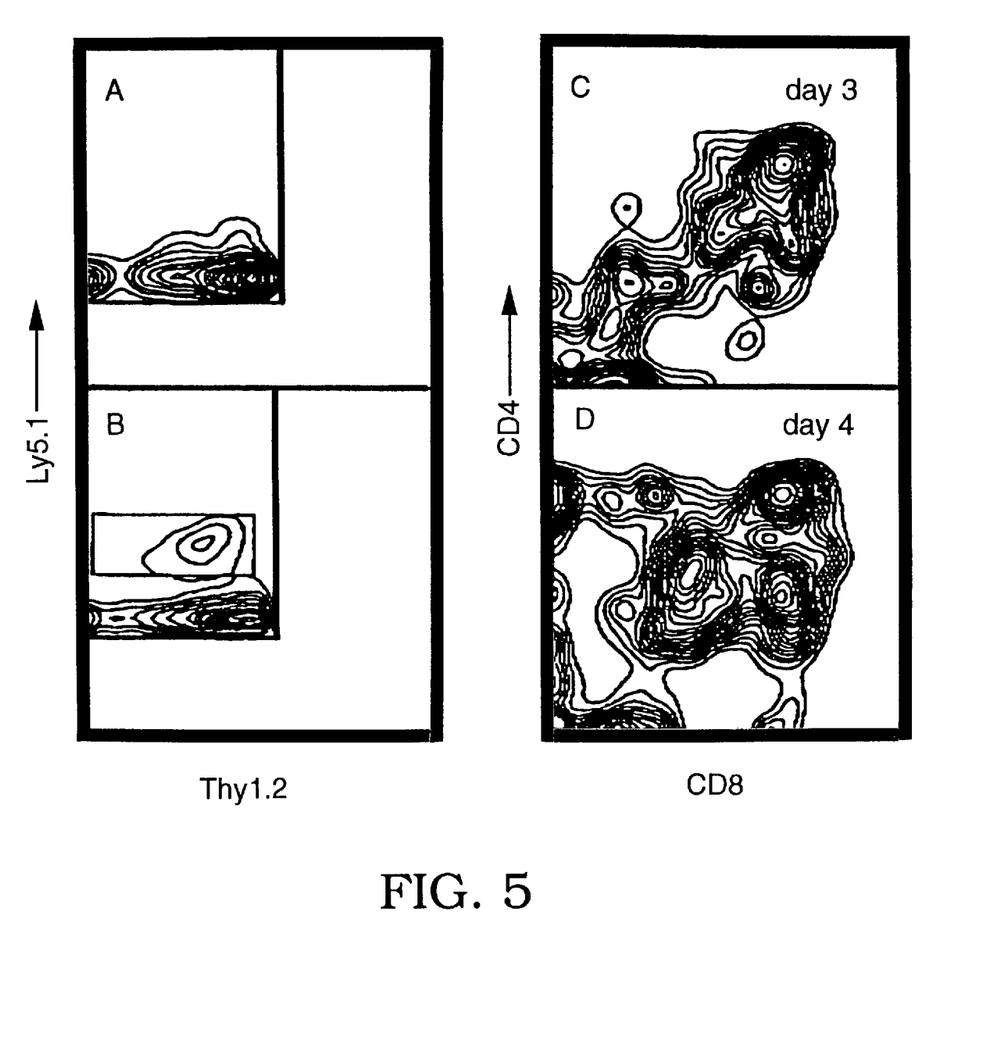
FIG. 5 shows the phenotype of $DP^{int}$ c-kit$^+$ thymocytes after differentiation in vivo.
Figure 6A:
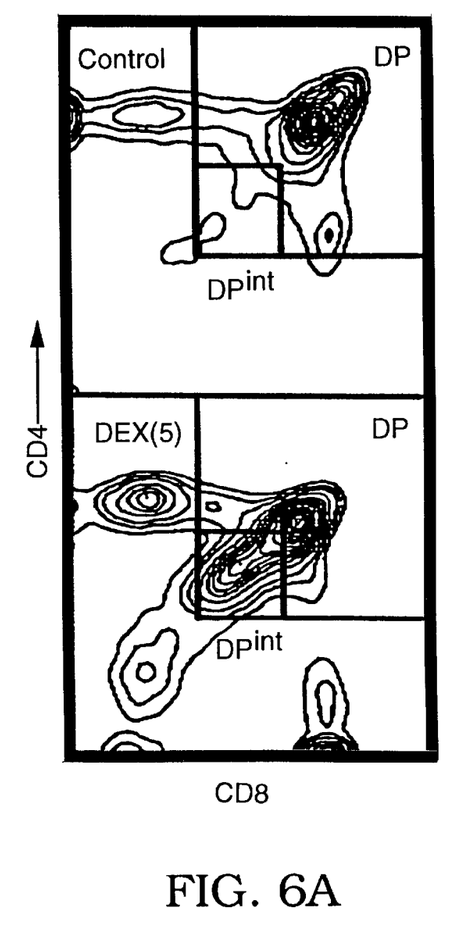
FIGS. 6A to 6E show the effect of dexamathasone injection on cell apoptosis and death of thymocyte subpopulations.
Figure 6B:
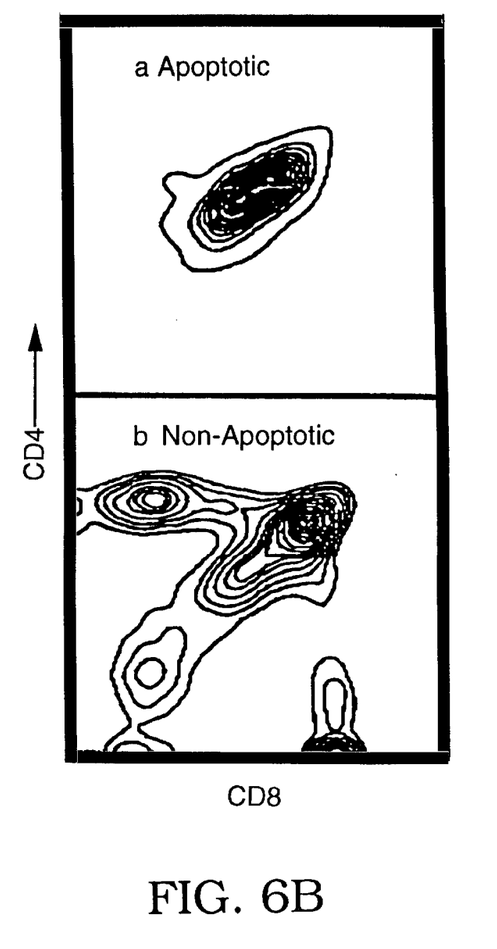
Figure 6C:
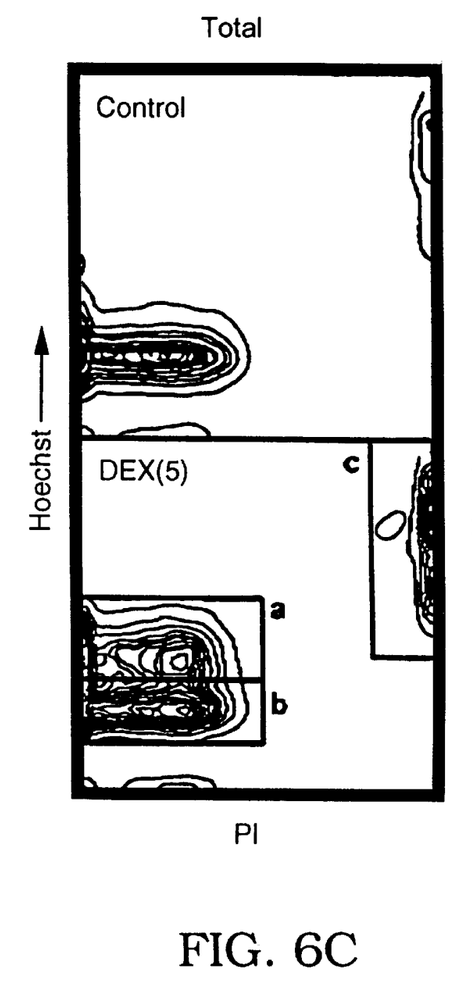
Figure 6D:
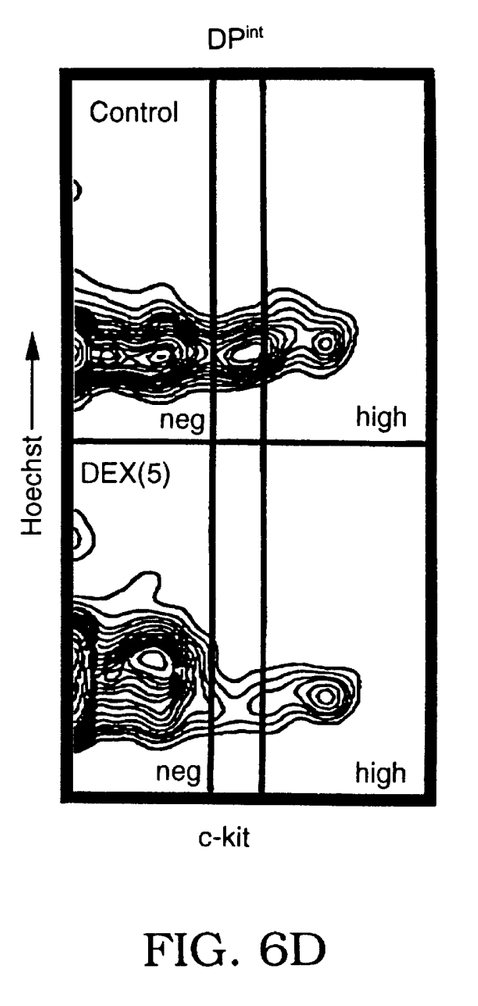
Figure 6E:
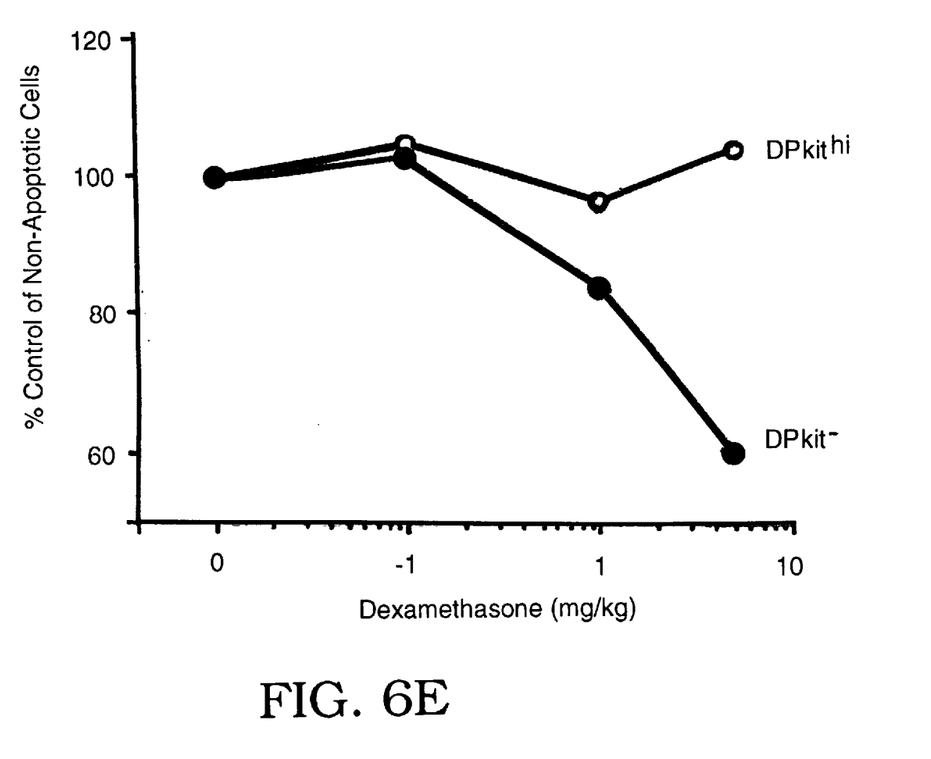

We also evaluated the differentiation potential of $DP^{int}$ c-kit$^{hi}$ thymocytes from C57BL6/Ka Thy 1.1 (Ly5.1;

Thy1.1) mice in vivo by using intrathymic injection into unirradiated congenic C57BL6 Ly5.2 (Ly5.2; Thy1.2) mice. FIG. 5A shows the profiles of the rare population of donor-derived cells detected four days after injection. The DP$^{int}$ c-kit$^{hi}$ blasts were mainly still in the DP stage three days after injection, but had differentiated into either CD4$^+$8$-$ or CD4$-$8$^+$ SP thymocytes after four days in vivo (FIG. 5B). There were no detectable numbers of donor-derived cells from a 3-fold higher number of injected DP$^{int}$ c-kit$-$ cells four days after injection.

Cells on The Maturation Pathway Express bcl-2, While Cells on The Default Pathway Do Not Bcl-2 is an anti-apoptosis protein, which when expressed in lymphocytes, makes them relatively resistant to various apoptosis-inducing stimuli, including corticosteroids. The expression of bcl-2, was striking in thymocyte subpopulations: the highest level was expressed in the DP$^{lo-int}$ c-kit$^{hi}$ populations, followed by CD4 SP cells. The cells in the default pathway DP$^{lo-int}$ c-kit$-$ (and most DP$^{hi}$ blasts) have low levels of bcl-2 protein, and DP small cells, which are destined to die, did not express measurable levels of bcl-2. Taken together, c-kit$^{hi}$ progenitor cells in the maturation pathway express protective bcl-2, while the DP$^{lo-int}$ c-kit$-$ cells and DP$^{hi}$ cells on the default pathway have down regulated the anti-apoptosis protein.

Cells in Default Pathway are Cortisone Sensitive, while those in the Maturation Pathway are Cortisone Resistant Because the level of glucocorticoids that are reached in the diurnal cycle are capable to include cell death in a significant fraction of thymocytes, it was tested whether death in the default pathway results from the action of corticosteroid. Previous study have shown that after in vivo administration of cortisone, the residual 2–5% of thymic lymphocytes are enriched for cells of the more mature phenotype, which at that time are largely found in the medulla. When 1 mg/kg of dexamethasone was injected (i.p.), total cellularity in the thymus decreased 3–4 fold by 24 h, probably due to a rapid phagocytosis by thymic macrophages. To evaluate apoptotic thymocytes including those in early phase of apoptosis by FACS, the thymus was analyzed 6 h after injection, when total cellularity did not decrease significantly. Cells induced to begin the stage of programmed cell death following treatment with dexamethasone are restricted to the c-kit$-$ population, and they distribute from DP$^{lo}$ to DP$^{hi}$ stages. Even at high doses of dexamethasone, the DP c-kit$^{hi}$ populations are resistant, while the c-kit$-$ cells are sensitive.

The above data demonstrate that only a tiny subset of double positive thymic blasts are progenitor cells—the DP$^{int}$ c-kit$^+$ cells. The differentiation of DP$^{int}$ c-kit$^+$ progenitors to single positive cells in vitro (the maturation pathway) depends on the presence of the HTSC; their differentiation to DP$^{hi}$ (c-kit$-$) blast cells (the default pathway) can occur in the absence of stroma. DP$^{int}$ c-kit$-$ blasts can become DP$^{hi}$ cells, but never differentiate to SP cells even in the presence of stroma. Accordingly, the DP$^{int}$ blast pool contains both c-kit$^+$ blasts with differentiating potential to SP cells and c-kit$-$ blasts whose progeny are destined to die. Positive and negative selection that involves DP$^{int}$ c-kit$^+$ blasts is an event that occurs in the presence of thymic stroma, whereas default to DP$^{hi}$ blast and small cells seems only to require nutrients in the medium.

Within 12 hours after addition of DP$^{int}$ c-kit$^+$ cells to HTSC, significant differentiation to single positive CD3hi cells has occurred. The rapid generation of SP cells from the DP$^{int}$ c-kit$^+$ progenitors goes through transitional intermediate of CD4$^+$8$^{med}$ c-kit$^+$ or CD4$^{med}$8$^+$c-kit$^+$ cells. The transitional intermediates that respond to HTSC are lineage committed, the CD4$^+$8$^{lo}$ for CD4 SP cells, and the CD4$^{lo}$8$^+$ for CD8 SP cells. The transitional intermediates are c-kit$^+$ and bcl-2$^{hi}$, and also express CD69.

DP$^{int}$ c-kit$-$ thymic blasts, almost 30% of which were also in cell cycle, could generate DP$^{hi}$ cells, but could not differentiate further. This suggests that they have already entered the default pathway, although their immediate progenitors are not yet revealed.

In the present study, 6 h after in vivo administration of glucocorticoid, when the size of thymus had not yet decreased, numerous apoptotic cells appeared that were DP$^{lo}$ to DP$^{hi}$. This relatively lower expression of CD4 and CD8 is probably due to a loss of these co-receptors on dying DP$^{hi}$ cells. These apoptotic cells were rapidly removed by thymic macrophage within 24 h. In the normal thymus, apoptotic DP thymocytes on the default pathway are likely to be incessantly removed by macrophage. The appearance of apoptotic small DN to DP$^{int}$ cells after the culture of DP$^{int}$ c-kit$^+$ cells was possibly due to a lack of sufficient phagocytotic cells in vitro.

The default differentiation pathway of DP$^{int}$ involves down regulation of Slf, IL-2 and IL-7 cytokine receptors, and up regulation of CD4 and CD8 co-receptors in situ. Down regulation of bcl-2 occurs along with this pathway. Presumably, this drop in bcl-2 expression signals a hyper-susceptibility to apoptois inducing agents, the most important of which is very likely endogenous glucocorticoids. c-kit$^+$ cells, which express high levels of bcl-2, are relatively resistant to corticosteroid. Furthermore, bcl-2 expression in DP$^{int}$ c-kit$^+$ blasts suggests their durability through the positive selection process. It appears that the expression of CD4 and CD8 continue to increase in cells that will end up either in the default pathway (DP$^{hi}$ small) or a positive selection pathway, and that positive selection involves, at least, cessation of transcription and translation of the unused CD4 or CD8 receptor.

In the present study, no clear function for c-kit in the maturation of the thymocytes has been demonstrated. Both addition of Slf or IL-7, and pretreatment with neutralizing IL-7 and IL-7R antibodies, did not affect maturation of DP$^{int}$ c-kit$^+$ cells in the presence of stroma.

The fact that the positive selection pathway from DP$^{int}$ c-kit$^+$ cells occurs on HTSC cells in vitro in $\leq$12 hours allows elucidation of events in the positive and negative selection pathways. Addition or elimination of FACS purified thymic stromal cells from genetically defined donors specifying particular TCR subsets to undergo section will enable isolation of the relevant cells for positive selection to antigens. Such cells are valuable for understanding the nature of the self-MHC$^+$/- peptide necessary for positive section, the kinds of cytokine or cell membrane signals provided by the relevant stromal cells, and the types of signal transduction pathways triggered in the DP$^{int}$ c-kit$^+$ progenitor to undergo either positive section, entry into the default pathway; or negative selection.

It is evident from the above results that the subject invention provides for the identification and isolation of a first population of thymocytes characterized as c-kit$^+$, CD4$^{int}$, and CD8$^{int}$ having T cell progenitor activity. These cells rapidly ($\leq$12 hours) respond to thymic stromal cultures to enter the positive selection, or maturation pathway. Cells in the maturation pathway are cortisone resistant, while cells in the default pathway enter apoptosis following glucocorticoid uptake. A second, more primitive thymocyte population is also identified, as having the phenotype of DP$^{lo}$, c-kit positive. A substantially enriched population of the subject thymocytes may be produced for a variety of purposes. The cells may be used in progenitor cell transplants, where is it necessary to provide T cell function. In addition, the cells may be modified by genetic engineering to provide capabilities naturally lacking in the cells.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A population of mammalian T lineage progenitor cells, wherein at least 95% of the cells in said population are thymocyte blast cells characterized as expressing intermediate levels of CD8, intermediate levels of CD4 and high levels of c-kit, wherein said cells express high levels of bcl-2.

2. A method of enrichment to provide a population of mammalian T lineage progenitor cells, wherein at least 95% of the cells in said population are thymocytes characterized as expressing intermediate levels of CD8, intermediate levels of CD4 and high levels of c-kit, the method comprising:

combining thymocytes with antibodies that specifically recognize each of c-kit, CD4, and CD8; and selecting by flow cytometry for blast cells that express intermediate levels of CD8, intermediate levels of CD4 and high levels of c-kit, wherein said cells express high levels of bcl-2, to provide a population of mammalian T lineage progenitor cells.

3. A method according to claim 2, wherein said antibodies are conjugated to fluorochromes.

4. A method according to claim 2 wherein said blast cells are initially separated by elutriation.

5. A population of mammalian T lineage progenitor cells, wherein at least 95% of the cells in said population are thymocyte blast cells characterized as expressing low levels of CD8, low levels of CD4 and high levels of c-kit, wherein said cells express high levels of bcl-2.

6. A method of enrichment to provide a population of mammalian T lineage progenitor cells, wherein at least 95% of the cells in said population are thymocytes characterized as expressing low levels of CD8, low levels of CD4 and high levels of c-kit, the method comprising:

combining thymocytes with antibodies that specifically recognize each of c-kit, CD4, and CD8; and selecting by flow cytometry for those blast cells that express low levels of CD8, low levels of CD4 and high levels of c-kit, wherein said cells express high levels of bcl-2. to provide a population of mammalian T lineage progenitor cells.

7. A method according to claim 6, wherein said antibodies are conjugated to fluorochromes.

8. A method according to claim 6, wherein said blast cells are initially separated by elutriation.

* * * * *